US012588896B2

(12) United States Patent     (10) Patent No.:   US 12,588,896 B2
Koshino     (45) Date of Patent:    Mar. 31, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riko Koshino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 18/046,869

(22) Filed: Oct. 14, 2022

(65) Prior Publication Data

US 2023/0157670 A1     May 25, 2023

(30) Foreign Application Priority Data

Nov. 25, 2021    (JP) ................................. 2021-191295

(51) Int. Cl.
*A61B 8/00*      (2006.01)
*A61B 8/08*      (2006.01)

(52) U.S. Cl.
CPC ............ *A61B 8/469* (2013.01); *A61B 8/0841* (2013.01); *A61B 8/085* (2013.01); *A61B 8/463* (2013.01); *A61B 8/0825* (2013.01)

(58) Field of Classification Search
CPC ..... A61B 8/0825; A61B 8/0841; A61B 8/085; A61B 8/463; A61B 8/469; A61B 8/483; A61B 8/5207
See application file for complete search history.

(56) References Cited

U.S. PATENT DOCUMENTS 6,733,458 B1   5/2004   Steins et al.
2003/0093008 A1*   5/2003   Van Bladel ............ A61B 18/02
                                                    600/567

(Continued)

FOREIGN PATENT DOCUMENTS

JP       2000107178 A   *   4/2000
JP       2004-208859 A     7/2004

(Continued)

OTHER PUBLICATIONS

Translated Takeda JP 2000107178 (Year: 2000).*

(Continued)

*Primary Examiner* — Anne M Kozak
*Assistant Examiner* — Brooke Lyn Klein
(74) *Attorney, Agent, or Firm* — Studebaker Brackett PLLC

(57) ABSTRACT

An ultrasound diagnostic apparatus includes an image acquisition unit that acquires an ultrasound image in which a breast of a subject is captured; a sampling target region detection unit that detects a sampling target region in which a tissue is sampled from the subject by a tissue sampling needle on the basis of the ultrasound image; a recommended path calculation unit that calculates a recommended path of the tissue sampling needle passing through the sampling target region; a monitor that displays the ultrasound image and the recommended path in a superimposed manner; a needle detection unit that detects the pierced tissue sampling needle on the basis of the ultrasound image; and a needle passage determination unit that determines whether or not the pierced tissue sampling needle has passed through the sampling target region.

17 Claims, 11 Drawing Sheets

(56) References Cited

U.S. PATENT DOCUMENTS

| | | | |
|---|---|---|---|
| 2003/0135119 A1* | 7/2003 | Lee | G01S 15/8993 600/461 |
| 2005/0033160 A1* | 2/2005 | Yamagata | A61B 6/12 600/425 |
| 2007/0270687 A1* | 11/2007 | Gardi | G06T 7/254 600/425 |
| 2008/0287827 A1 | 11/2008 | Sarkar et al. | |
| 2009/0198094 A1 | 8/2009 | Fenster et al. | |
| 2011/0087132 A1* | 4/2011 | DeFreitas | A61B 10/0233 378/62 |
| 2011/0230768 A1 | 9/2011 | Nir et al. | |
| 2013/0274608 A1* | 10/2013 | Takeda | A61B 8/4444 600/461 |
| 2014/0039316 A1 | 2/2014 | Ichioka et al. | |
| 2015/0265251 A1* | 9/2015 | Cho | G06T 7/143 600/437 |
| 2017/0196535 A1 | 7/2017 | Arai et al. | |
| 2017/0340307 A1 | 11/2017 | Kano | |
| 2018/0000446 A1 | 1/2018 | Lu et al. | |
| 2018/0308247 A1* | 10/2018 | Gupta | G06T 7/62 |
| 2018/0342060 A1* | 11/2018 | Yao | G06N 3/045 |
| 2020/0345325 A1 | 11/2020 | Tahmasebi Maraghoosh et al. | |
| 2021/0000553 A1 | 1/2021 | St. Pierre | |
| 2021/0259660 A1 | 8/2021 | Bharat et al. | |

FOREIGN PATENT DOCUMENTS

| | | | | |
|---|---|---|---|---|
| JP | 2012-511941 A | | 5/2012 | |
| JP | 2013-192627 A | | 9/2013 | |
| JP | 2013-240369 A | | 12/2013 | |
| JP | 2014054386 A | * | 3/2014 | |
| JP | 2017-209324 A | | 11/2017 | |
| JP | 2017-209325 A | | 11/2017 | |
| JP | 2017-209326 A | | 11/2017 | |
| JP | 2020-044045 A | | 3/2020 | |
| JP | 2021007659 A | * | 1/2021 | |
| JP | 2021-520935 A | | 8/2021 | |
| KR | 20200006886 A | * | 1/2020 | |
| WO | 2014/003070 A1 | | 1/2014 | |

OTHER PUBLICATIONS

Translated Nemoto JP 2021007659 (Year: 2021).*

Translated JP2014054386 (Year: 2014).*

Translated Park KR 20200006886 (Year: 2020).*

The extended European search report issued by the European Patent Office on Apr. 19, 2023, which corresponds to European Patent Application No. 22202281.6-1126 and is related to U.S. Appl. No. 18/046,869.

An Office Action; "Notice of Reasons for Refusal," mailed by the Japanese Patent Office on Apr. 1, 2025, which corresponds to Japanese Patent Application No. 2021-191295 and is related to U.S. Appl. No. 18/046,869; with English language translation.

Communication pursuant to Article 94(3) EPC issued by the European Patent Office on Apr. 2, 2025, which corresponds to European Patent Application No. 22202281.6-1122 and is related to U.S. Appl. No. 18/046,869.

An Office Action; "Decision of Refusal," mailed by the Japanese Patent Office on Jun. 24, 2025, which corresponds to Japanese Patent Application No. 2021-191295 and is related to U.S. Appl. No. 18/046,869; with English language translation.

* cited by examiner

```
SAMPLING
TARGET REGION
DETECTION UNIT                                        — 35

┌────────────────────────────┐
            │    MALIGNANCY              │  — 54
            │ DETERMINATION UNIT         │
            └────────────────────────────┘

┌────────────────────────────┐
            │  REGION EXTRACTION         │  — 55
            │        UNIT                │
            └────────────────────────────┘
```

FIG. 14

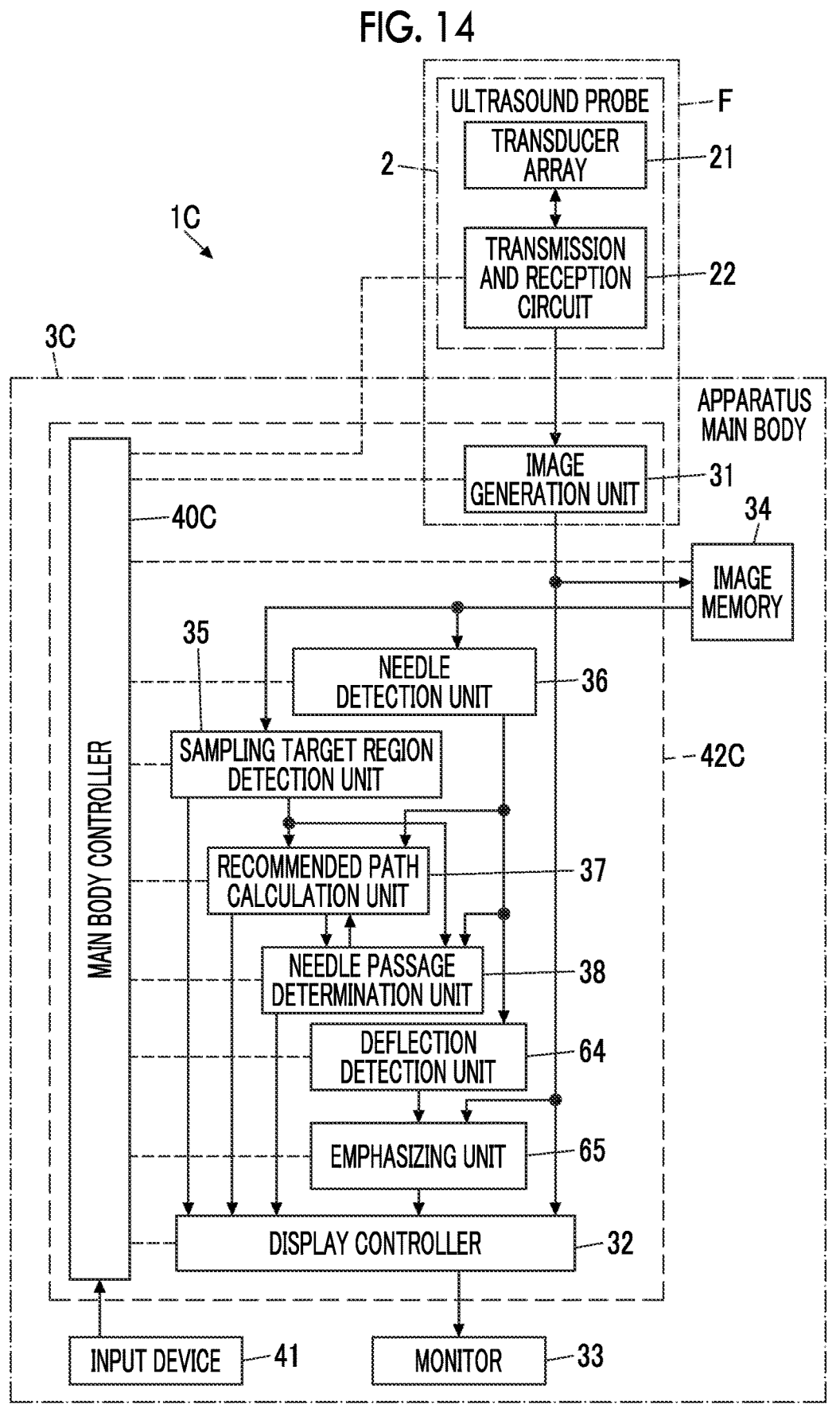

```
                              ┌──────────────────────────────┐
                              │  ULTRASOUND PROBE      ──── F │
                              │   ┌─────────────────┐         │
                              │   │   TRANSDUCER    │ ──── 21 │
                              │   │     ARRAY       │         │
                2 ───┐        │   └─────────────────┘         │
                              │         ↕                     │
                              │   ┌─────────────────┐         │
                              │   │  TRANSMISSION   │         │
         1C                   │   │  AND RECEPTION  │ ──── 22 │
          ↘                   │   │    CIRCUIT      │         │
                              │   └─────────────────┘         │
                              └──────────────────────────────┘

3C                                              APPARATUS
                                                   MAIN BODY

┌─────────────────┐
                     │     IMAGE       │ ──── 31
          40C        │ GENERATION UNIT │
                     └─────────────────┘                      ┌──────────┐
                                                        34 ──│  IMAGE   │
                                                              │  MEMORY  │
                                                              └──────────┘
        35
                     ┌─────────────────┐
                     │     NEEDLE      │ ──── 36
                     │ DETECTION UNIT  │
                     └─────────────────┘
         │
  M      │  ┌─────────────────────────┐
  A      │  │ SAMPLING TARGET REGION  │                    42C
  I      │  │    DETECTION UNIT       │
  N      │  └─────────────────────────┘
         │
  B      │  ┌─────────────────────────┐
  O      │  │   RECOMMENDED PATH      │ ──── 37
  D      │  │   CALCULATION UNIT      │
  Y      │  └─────────────────────────┘
         │
  C      │  ┌─────────────────────────┐
  O      │  │    NEEDLE PASSAGE       │ ──── 38
  N      │  │  DETERMINATION UNIT     │
  T      │  └─────────────────────────┘
  R      │
  O      │  ┌─────────────────────────┐
  L      │  │     DEFLECTION          │ ──── 64
  L      │  │   DETECTION UNIT        │
  E      │  └─────────────────────────┘
  R      │
         │  ┌─────────────────────────┐
         │  │    EMPHASIZING UNIT     │ ──── 65
         │  └─────────────────────────┘
         │
         │  ┌──────────────────────────────────┐
         │  │      DISPLAY CONTROLLER          │ ──── 32
         │  └──────────────────────────────────┘

┌──────────────┐                    ┌──────────────┐
   │ INPUT DEVICE │ ──── 41            │   MONITOR    │ ──── 33
   └──────────────┘                    └──────────────┘
```

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2021-191295 filed on Nov. 25, 2021. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which are used in an examination of a breast of a subject.

2. Description of the Related Art

In the related art, in order to perform a biopsy on a breast of a subject, a procedure of piercing the breast with a tissue sampling needle while observing the inside of the breast of the subject using a so-called ultrasound diagnostic apparatus has been performed. In such a procedure, for example, a technique as disclosed in JP2021-520935A has been developed so that an examiner can easily reach a target location in the subject with the tissue sampling needle. JP2021-520935A discloses predicting a needle reach position on the basis of characteristics of a tissue sampling needle and tissue characteristics of a subject such as a mammary gland tissue and an adipose tissue in the breast. In JP2021-520935A, the tissue characteristics of the subject are determined by image analysis of an ultrasound image or an input of information by the examiner.

SUMMARY OF THE INVENTION

However, in the technology disclosed in JP2021-520935A, since the reach position of the tissue sampling needle is predicted on the basis of the characteristics of the tissue sampling needle and the tissue characteristics of a patient determined by the image analysis or the input by the examiner, the predicted reach position of the tissue sampling needle may deviate from the actual reach position of the tissue sampling needle, and it may be difficult for a distal end of the tissue sampling needle to reach the target location unless the examiner is skilled.

The present invention has been made in order to solve such a problem in the related art, and an object of the present invention is to provide an ultrasound diagnostic apparatus and a control method of the ultrasound diagnostic apparatus which can reliably perform a biopsy in a short time even by an unskilled examiner.

In order to achieve the object, an ultrasound diagnostic apparatus according to an aspect of the present invention comprises an image acquisition unit that acquires an ultrasound image in which a breast of a subject is captured; a sampling target region detection unit that detects a sampling target region in which a tissue is sampled from the subject by a tissue sampling needle on the basis of the ultrasound image; a recommended path calculation unit that calculates a recommended path of the tissue sampling needle passing through the sampling target region; a monitor that displays the ultrasound image and the recommended path in a superimposed manner; a needle detection unit that detects the pierced tissue sampling needle on the basis of the ultrasound image; and a needle passage determination unit that determines whether or not the pierced tissue sampling needle has passed through the sampling target region.

The sampling target region detection unit can have a malignancy determination unit that determines malignancy in each portion in a region of interest of the breast of the subject, and a region extraction unit that extracts a region in which the malignancy determined by the malignancy determination unit is equal to or greater than a predetermined threshold value, as the sampling target region.

The malignancy determination unit can display a determination result of the malignancy on the monitor.

In this case, the malignancy determination unit can display a heat map of the determined malignancy as the determination result on the monitor.

The recommended path calculation unit can detect pectoralis major muscle of the subject on the basis of the ultrasound image, and calculate a path that passes through the sampling target region and is parallel to the pectoralis major muscle, as the recommended path until the tissue sampling needle is detected by the needle detection unit.

In a case where a length of the tissue sampling needle, which is detected by the needle detection unit, having passed through an inside of the sampling target region is equal to or greater than a predetermined ratio with respect to a length of the recommended path in the sampling target region, the needle passage determination unit can determine that the tissue sampling needle has passed through the sampling target region.

The ultrasound diagnostic apparatus can further comprise a warning unit that issues a warning in a case where it is predicted that the tissue sampling needle detected by the needle detection unit advances toward pectoralis major muscle of the subject.

The ultrasound diagnostic apparatus can further comprise a final point reach determination unit that determines whether or not the tissue sampling needle has reached a piercing final point on the basis of the detection of the tissue sampling needle by the needle detection unit.

In this case, the ultrasound diagnostic apparatus can further comprise an examination result memory that stores the ultrasound image acquired by the image acquisition unit before the tissue sampling needle passes through the sampling target region, the ultrasound image, which is acquired by the image acquisition unit, at a time when the final point reach determination unit determines that the tissue sampling needle has reached the final point, coordinates of the tissue sampling needle detected by the needle detection unit or the ultrasound image of the tissue sampling needle detected by the needle detection unit, and the ultrasound image including the sampling target region acquired by the image acquisition unit after the tissue sampling needle is pulled out from the subject.

The image acquisition unit can acquire the ultrasound image in both a cross section including the recommended path and a cross section orthogonal to the cross section including the recommended path.

Further, the image acquisition unit can acquire a three-dimensional ultrasound image.

In this case, the sampling target region detection unit can calculate a volume of the detected sampling target region, and display the volume on the monitor.

The sampling target region detection unit can detect the sampling target region on the basis of the ultrasound image acquired by the image acquisition unit before the piercing of the tissue sampling needle, and detect again the sampling target region on the basis of the ultrasound image acquired by the image acquisition unit after the tissue sampling needle retreats from the sampling target region.

The ultrasound diagnostic apparatus can further comprise a deflection detection unit that detects deflection occurring in a path through which the tissue sampling needle has passed in the ultrasound image on the basis of the detection of the tissue sampling needle by the needle detection unit; and an emphasizing unit that emphasizes a continuous region having a brightness value within a predetermined range for a brightness value of the ultrasound image for a position where the deflection is detected by the deflection detection unit, as a deflection occurrence region, and displays the deflection occurrence region on the monitor.

A control method of an ultrasound diagnostic apparatus according to another aspect of the present invention comprises acquiring an ultrasound image in which a breast of a subject is captured; detecting a sampling target region in which a tissue is sampled from the subject by a tissue sampling needle on the basis of the ultrasound image; calculating a recommended path of the tissue sampling needle passing through the sampling target region; displaying the ultrasound image and the recommended path on a monitor in a superimposed manner; detecting the pierced tissue sampling needle on the basis of the ultrasound image; and determining whether or not the pierced tissue sampling needle has passed through the sampling target region.

According to the present invention, since an ultrasound diagnostic apparatus comprises an image acquisition unit that acquires an ultrasound image in which a breast of a subject is captured; a sampling target region detection unit that detects a sampling target region in which a tissue is sampled from the subject by a tissue sampling needle on the basis of the ultrasound image; a recommended path calculation unit that calculates a recommended path of the tissue sampling needle passing through the sampling target region; a monitor that displays the ultrasound image and the recommended path in a superimposed manner; a needle detection unit that detects the pierced tissue sampling needle on the basis of the ultrasound image; and a needle passage determination unit that determines whether or not the pierced tissue sampling needle has passed through the sampling target region, a biopsy can be reliably performed in a short time even by an unskilled examiner.

4

Figure 6:
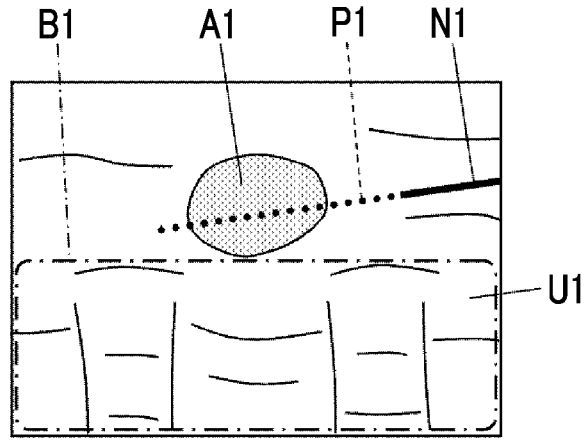

FIG. 6 is a diagram illustrating an example of a recommended path corrected in the first embodiment of the present invention.

Figure 7:
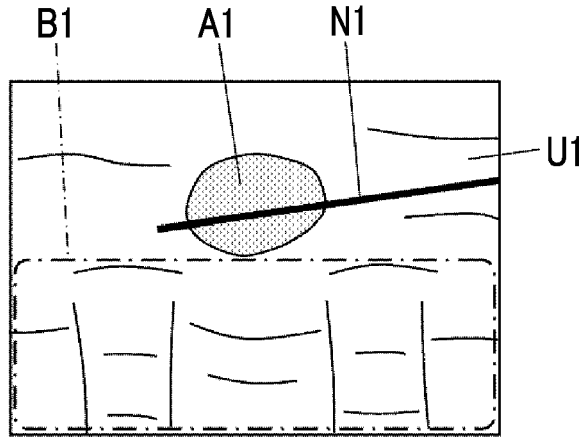

FIG. 7 is a diagram illustrating an example of a tissue sampling needle that has reached a piercing final point, which is depicted on an ultrasound image in the first embodiment of the present invention.

Figure 8:
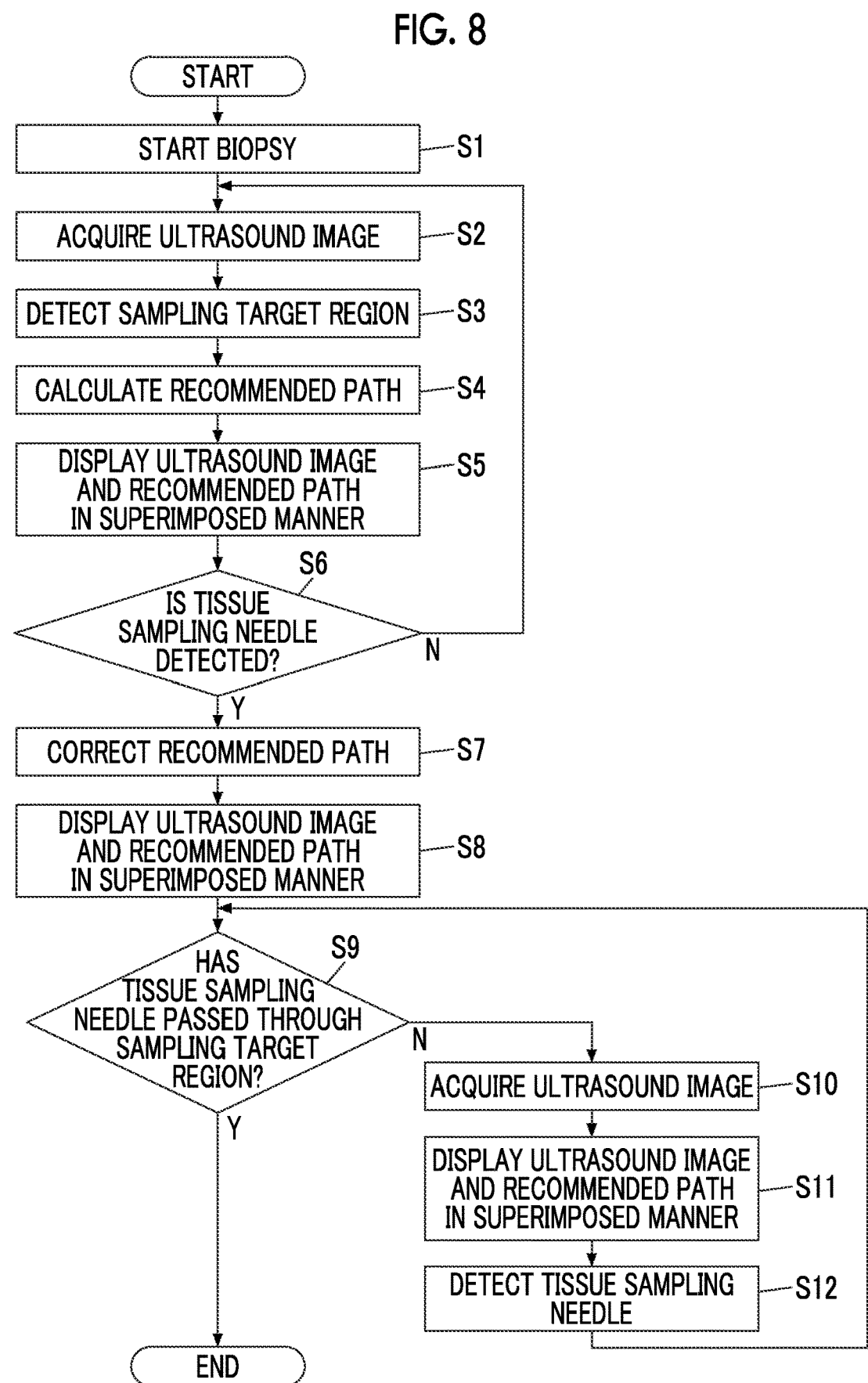

FIG. 8 is a flowchart illustrating an operation of the ultrasound diagnostic apparatus according to the first embodiment of the present invention.

Figure 9:
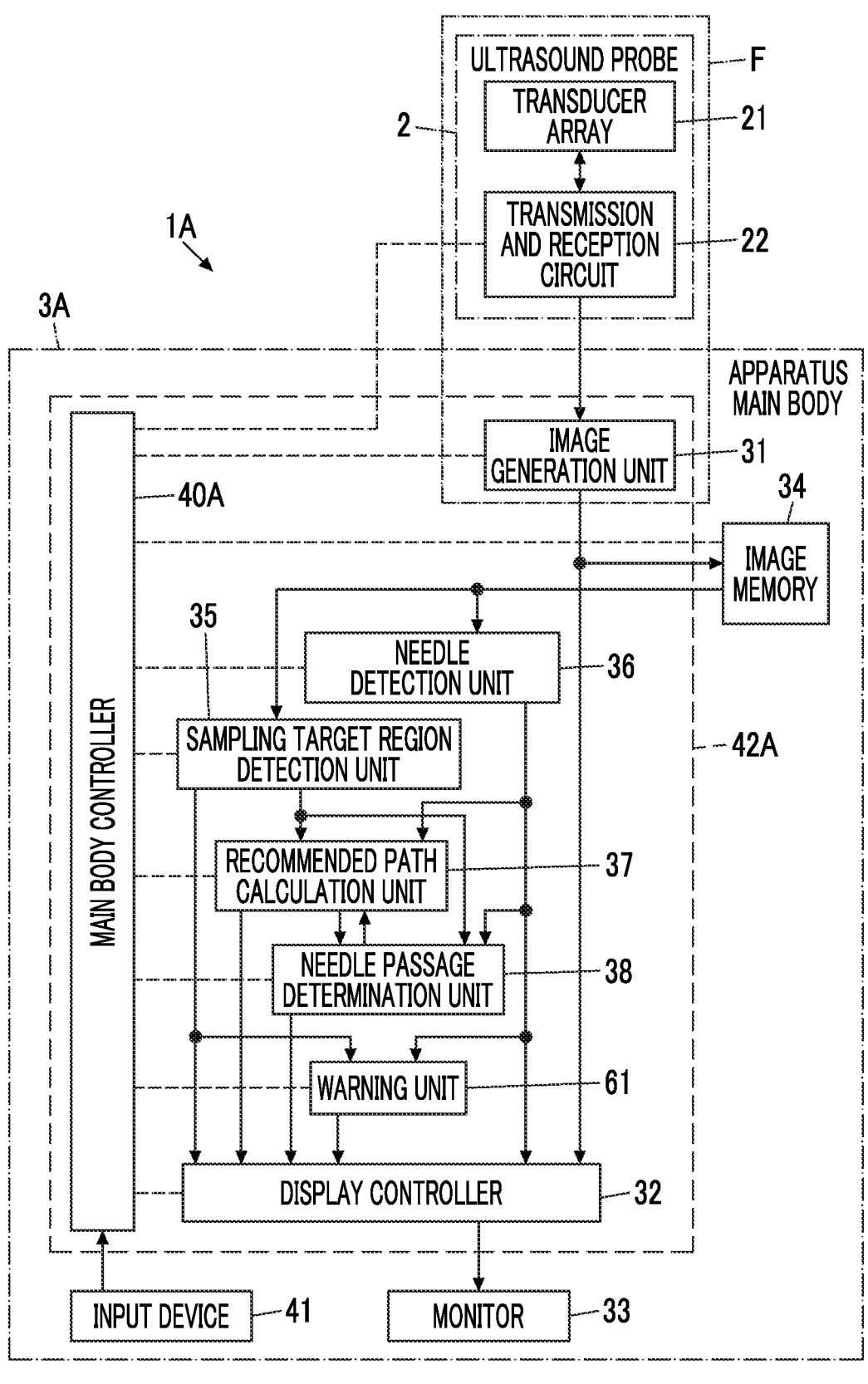

FIG. 9 is a block diagram illustrating a configuration of an ultrasound diagnostic apparatus according to a second embodiment of the present invention.

Figure 10:
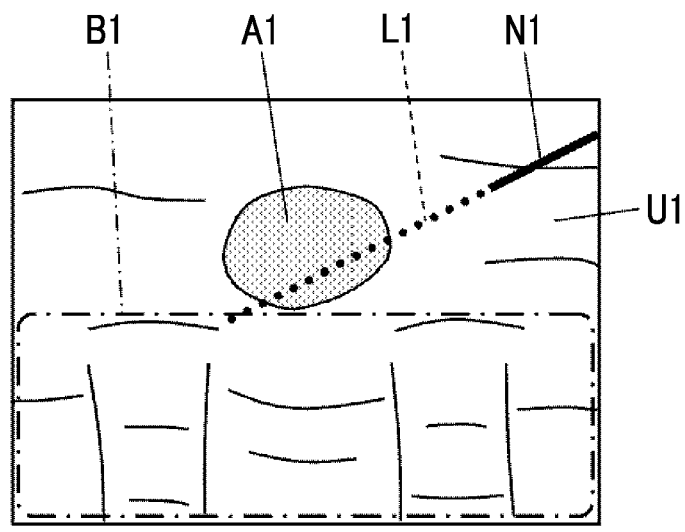

FIG. 10 is a diagram illustrating an example of a tissue sampling needle predicted to advance toward the pectoralis major muscle in the second embodiment of the present invention.

Figure 11:
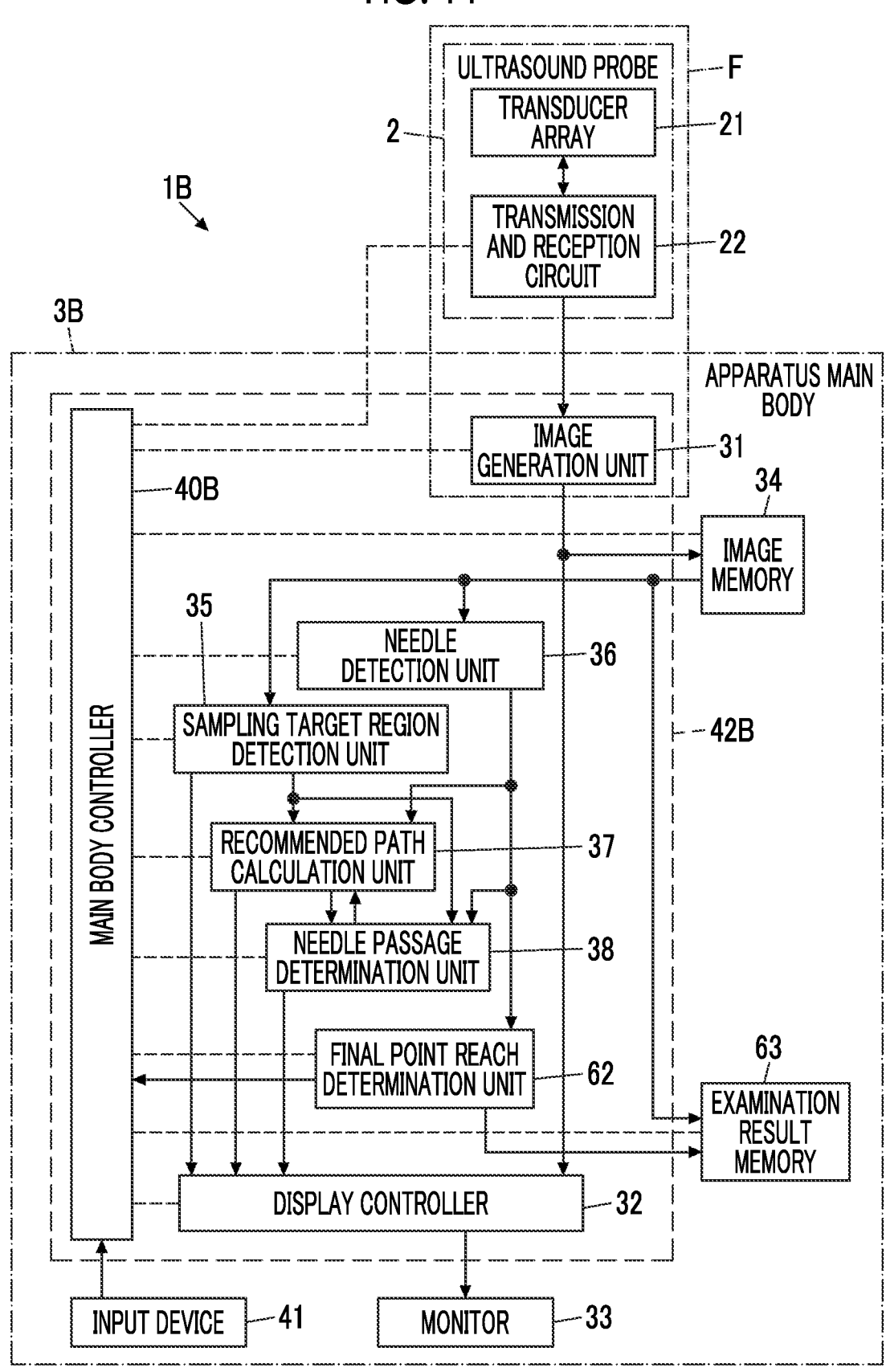

FIG. 11 is a block diagram illustrating a configuration of an ultrasound diagnostic apparatus according to a third embodiment of the present invention.

Figure 12:
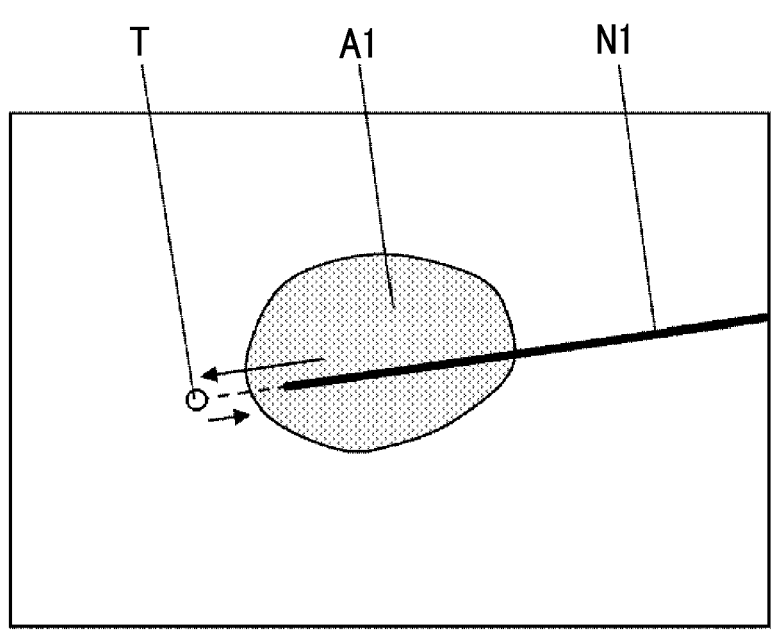

FIG. 12 is a diagram schematically illustrating an example of a final point of the tissue sampling needle in the third embodiment of the present invention.

Figure 13:
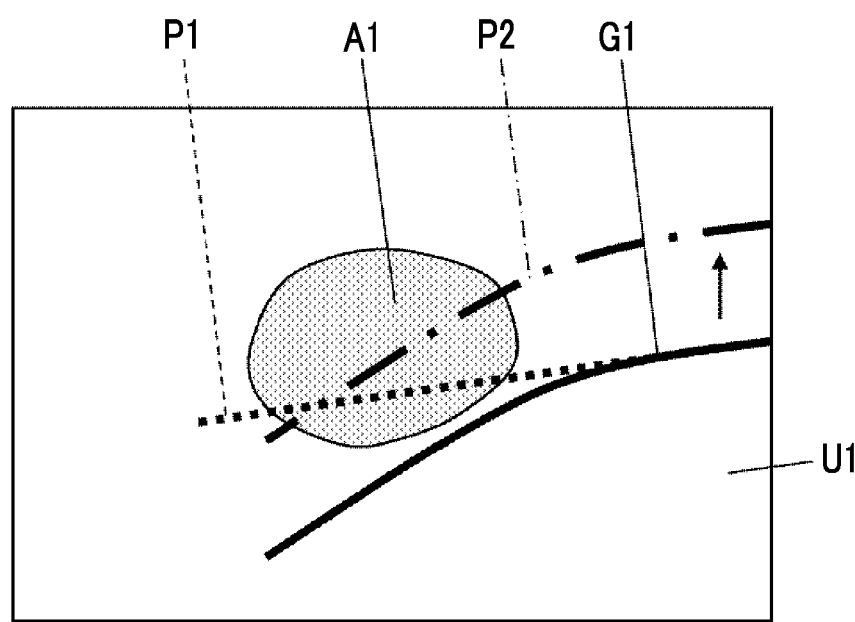

FIG. 13 is a diagram illustrating an example of a recommended path corrected in the third embodiment of the present invention.

FIG. 14 is a block diagram illustrating a configuration of an ultrasound diagnostic apparatus according to a fourth embodiment of the present invention.

Figure 15:
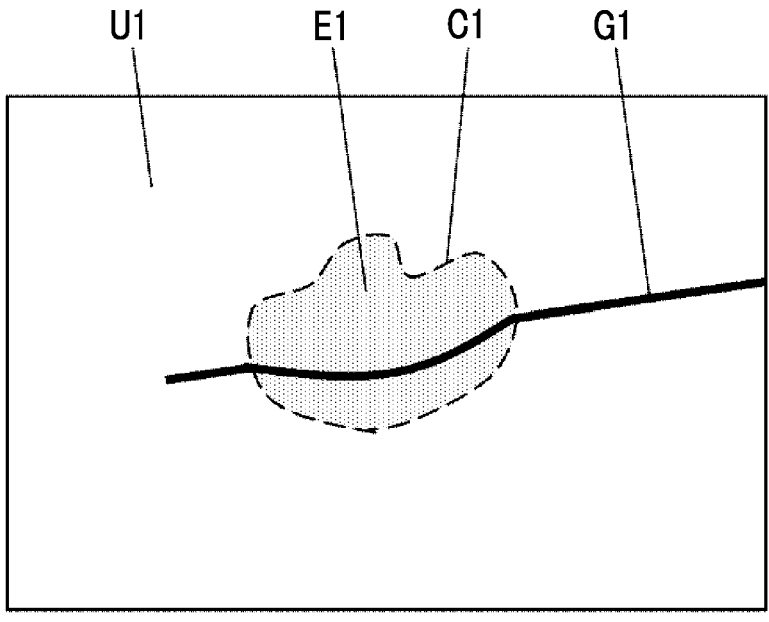

FIG. 15 is a diagram illustrating an example of a deflection occurrence region in the fourth embodiment of the present invention.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
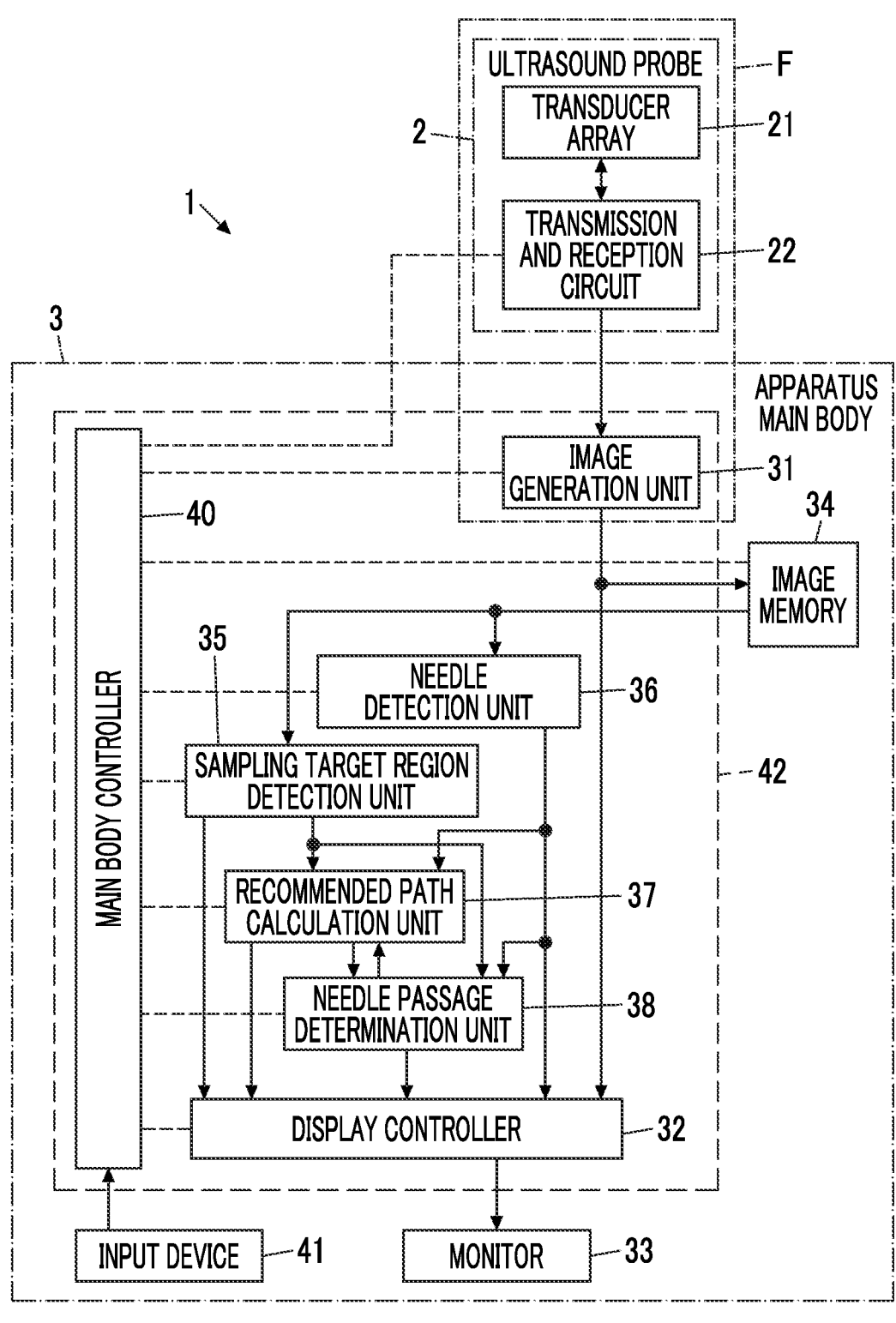
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 comprises an ultrasound probe 2, and an apparatus main body 3 connected to the ultrasound probe 2. The ultrasound diagnostic apparatus 1 is used to observe a tissue sampling needle that is pierced into the breast of a subject and a sampling target region suspected to be a lesion part in a case of performing a biopsy of the breast of the subject. Here, the tissue sampling needle refers to a needle-like instrument used to sample a tissue in the subject. Further, the sampling target region refers to a region which is suspected to be, for example, a lesion part, and in which a target tissue to be sampled by the tissue sampling needle is present.

The ultrasound probe 2 comprises a transducer array 21, and a transmission and reception circuit 22 is connected to the transducer array 21.

The apparatus main body 3 comprises an image generation unit 31, and the image generation unit 31 is connected to the transmission and reception circuit 22 of the ultrasound probe 2. The transducer array 21 and the transmission and reception circuit 22 of the ultrasound probe 2, and the image generation unit 31 of the apparatus main body 3 constitute an image acquisition unit F.

Further, a display controller 32 and a monitor 33 are sequentially connected to the image generation unit 31. An image memory 34 is connected to the image generation unit 31. Further, a sampling target region detection unit 35 and a needle detection unit 36 are connected to the image memory 34. A recommended path calculation unit 37 and a needle passage determination unit 38 are connected to the sampling target region detection unit 35. Similarly to the sampling target region detection unit 35, the recommended path calculation unit 37 and the needle passage determination unit 38 are also connected to the needle detection unit 36. The needle passage determination unit 38 is connected to the recommended path calculation unit 37. Further, each of the sampling target region detection unit 35, the needle detection unit 36, the recommended path calculation unit 37, and the needle passage determination unit 38 is connected to the display controller 32.

In addition, a main body controller 40 is connected to the transmission and reception circuit 22, the image generation unit 31, the display controller 32, the image memory 34, the sampling target region detection unit 35, the needle detection unit 36, the recommended path calculation unit 37, and the needle passage determination unit 38. An input device 41 is connected to the main body controller 40.

Further, the image generation unit 31, the display controller 32, the sampling target region detection unit 35, the needle detection unit 36, the recommended path calculation unit 37, the needle passage determination unit 38, and the main body controller 40 constitute a processor 42 for the apparatus main body 3.

The transducer array 21 of the ultrasound probe 2 has a plurality of ultrasonic transducers arranged in a one-dimensional or two-dimensional manner. According to a drive signal supplied from the transmission and reception circuit 22, each of the ultrasonic transducers transmits an ultrasonic wave and receives an ultrasound echo from the subject to output a signal based on the ultrasound echo. For example, each ultrasonic transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
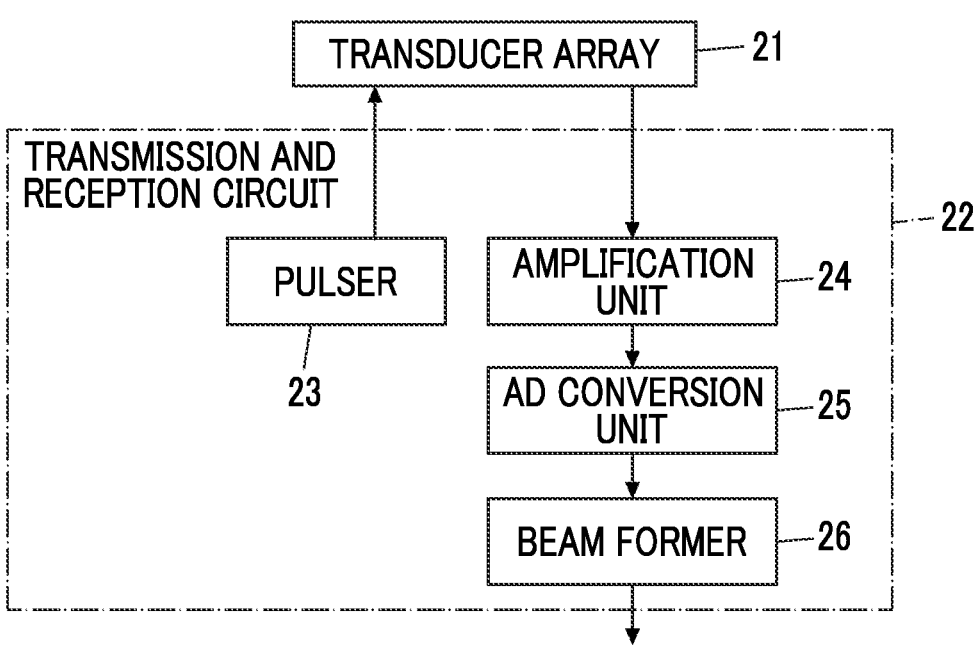
FIG. 2 is a block diagram illustrating a configuration of a transmission and reception circuit in the first embodiment of the present invention.

The transmission and reception circuit 22 causes the transducer array 21 to transmit the ultrasonic wave and generates a sound ray signal on the basis of a reception signal acquired by the transducer array 21, under the control of the main body controller 40. As illustrated in FIG. 2, the transmission and reception circuit 22 has a pulser 23 connected to the transducer array 21, and an amplification unit 24, an analog to digital (AD) conversion unit 25, and a beam former 26 that are sequentially connected in series from the transducer array 21.

The pulser 23 includes, for example, a plurality of pulse generators, and the pulser 23 adjusts the amount of delay of each drive signal so that ultrasonic waves transmitted from the plurality of ultrasonic transducers of the transducer array 21 form an ultrasound beam on the basis of a transmission delay pattern selected according to the control signal from the main body controller 40, and supplies the obtained signals to the plurality of ultrasonic transducers. Thus, in a case where a pulsed or continuous-wave voltage is applied to the electrodes of the ultrasonic transducers of the transducer array 21, the piezoelectric body expands and contracts to generate pulsed or continuous-wave ultrasonic waves from each ultrasonic transducer. From the combined wave of these ultrasonic waves, an ultrasound beam is formed.

The transmitted ultrasound beam is reflected by a target, for example, a site of the subject, and propagates toward the transducer array 21 of the ultrasound probe 2. The ultrasound echo propagating toward the transducer array 21 in this manner is received by each ultrasonic transducer constituting the transducer array 21. In this case, each ultrasonic transducer constituting the transducer array 21 expands and contracts by receiving the propagating ultrasound echo to generate a reception signal that is an electric signal, and outputs the reception signal to the amplification unit 24.

The amplification unit 24 amplifies the signals input from each ultrasonic transducer constituting the transducer array 21, and transmits the amplified signals to the AD conversion unit 25. The AD conversion unit 25 converts the signal transmitted from the amplification unit 24 into digital reception data. The beam former 26 performs so-called reception focusing processing in which addition is performed by giving delays to respective pieces of the reception data received from the AD conversion unit 25. Through the reception focusing processing, a sound ray signal in which each piece of the reception data converted by the AD conversion unit 25 is phased and added and the focus of the ultrasound echo is narrowed is acquired.

Figure 3:
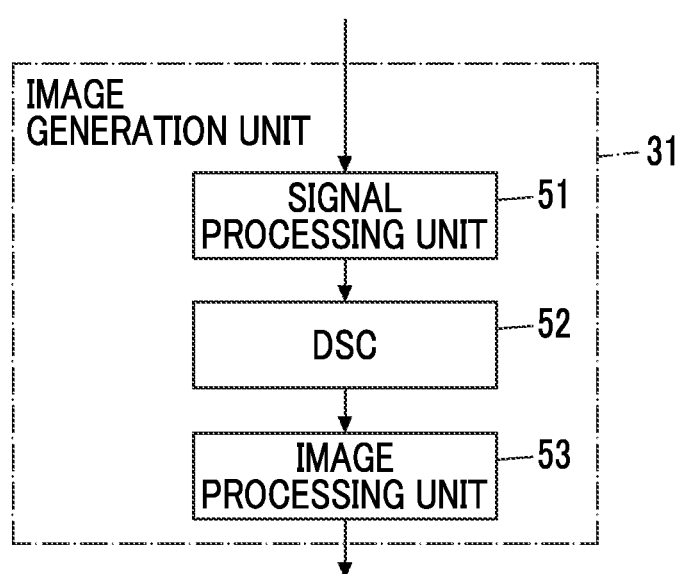
FIG. 3 is a block diagram illustrating a configuration of an image generation unit in the first embodiment of the present invention.

As illustrated in FIG. 3, the image generation unit 31 has a configuration in which a signal processing unit 51, a digital scan converter (DSC) 52, and an image processing unit 53 are sequentially connected in series.

The signal processing unit 51 generates a B-mode image signal, which is tomographic image information regarding tissues inside the subject, by performing, on the sound ray signal received from the transmission and reception circuit 22, correction of the attenuation due to the distance according to the depth of the reflection position of the ultrasonic wave using a sound speed value set by the main body controller 40 and then performing envelope detection processing.

The DSC 52 converts (raster conversion) the B-mode image signal generated by the signal processing unit 51 into an image signal according to a normal television signal scanning method.

The image processing unit 53 performs various kinds of necessary image processing such as gradation processing on the B-mode image signal input from the DSC 52, and then sends the B-mode image signal to the display controller 32 and the image memory 34. In the following, the B-mode image signal subjected to the image processing by the image processing unit 53 is simply referred to as an ultrasound image.

The main body controller 40 controls the transmission and reception circuit 22 of the ultrasound probe 2 and each unit of the apparatus main body 3 according to a program and the like recorded in advance.

The display controller 32 performs predetermined processing on the ultrasound image or the like generated by the image generation unit 31 and displays the ultrasound image or the like on the monitor 33, under the control of the main body controller 40.

The monitor 33 performs various kinds of display under the control of the display controller 32. The monitor 33 includes a display device such as a liquid crystal display (LCD), or an organic electroluminescence (EL) display.

The input device 41 is for a user to perform an input operation. The input device 41 is configured by, for example, a device for a user to perform an input operation, such as a keyboard, a mouse, a trackball, a touchpad, a touch panel, or the like.

Under the control of the main body controller 40, the image memory 34 stores the ultrasound image generated by the image generation unit 31, and sends the stored ultrasound image to the sampling target region detection unit 35 and the needle detection unit 36. Here, as the image memory 34, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), and a universal serial bus memory (USB memory) can be used.

Figure 4:
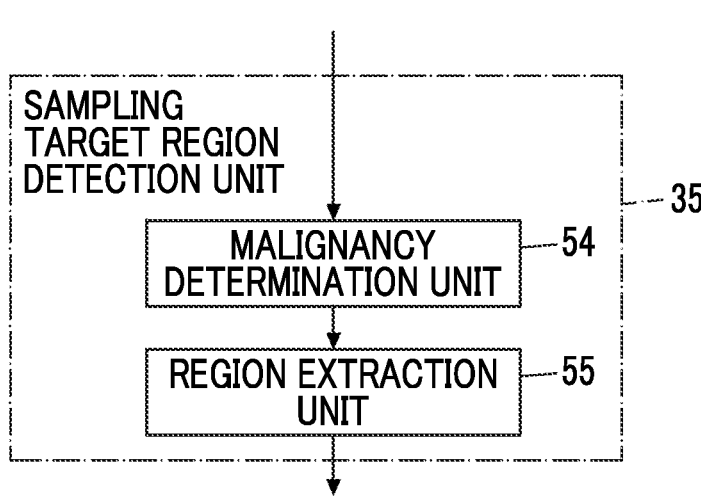
FIG. 4 is a block diagram illustrating a configuration of a sampling target region detection unit in the first embodiment of the present invention.

The sampling target region detection unit 35 detects a sampling target region in which a tissue is sampled from the subject by the tissue sampling needle, on the basis of the ultrasound image. As illustrated in FIG. 4, the sampling target region detection unit 35 has a configuration in which a malignancy determination unit 54 and a region extraction unit 55 are connected in series.

The malignancy determination unit 54 performs an image analysis of the ultrasound image of the breast of the subject to recognize a region suspected to be a lesion part such as a tumor, and sets a region of interest including the recognized region on the ultrasound image. Further, the malignancy determination unit 54 determines the malignancy of each portion in the region of interest of the breast of the subject.

Further, for example, the malignancy determination unit 54 can recognize the region suspected to be a lesion part on the ultrasound image by applying a method of using simple pattern matching, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012).

Here, for example, in general, it is said that benign tumors often have a circular or elliptical shape, and malignant tumors such as breast cancer often have a so-called lobed or polygonal shape. The malignancy determined by the malignancy determination unit 54 refers to a probability that the tissue in the set region of interest is malignant, and is calculated, for example, in units of pixels. For example, the higher the malignancy of the pixel, the higher the probability that the pixel represents a tissue in a malignant lesion part, and the lower the malignancy of the pixel, the higher the probability that the pixel represents a tissue in a benign lesion part.

The malignancy determination unit 54 determines the malignancy of the tissue in the region of interest by recognizing the shape of the tissue using, for example, an image recognition method including pattern matching and extraction of a so-called feature amount, or a deep learning method. For example, in a case of using a deep learning method, the malignancy determination unit 54 determines the malignancy in units of pixels by performing learning in advance using a plurality of ultrasound images including a malignant tumor and a plurality of ultrasound images including a benign tumor as so-called teacher data, and comparing a relationship between the brightness of a specific pixel in the set region of interest and the brightness of surrounding pixels with the learned data. In this case, the malignancy determination unit 54 displays a determination result of the malignancy on the monitor 33 as a so-called heat map in which colors are assigned to regions on the ultrasound image such that, for example, a region with a higher malignancy is colored red, and a region with a lower malignancy is colored blue.

The region extraction unit 55 has a predetermined threshold value regarding the malignancy, and determines whether or not the value of the malignancy determined by the malignancy determination unit 54 is equal to or greater than the predetermined threshold value. The region extraction unit 55 further extracts a region of which the value of the malignancy determined by the malignancy determination unit 54 is equal to or greater than the predetermined threshold value, as a sampling target region. Therefore, the sampling target region is a region including, for example, a set of pixels having a malignancy equal to or greater than the predetermined threshold value in the region suspected to be a lesion part such as a tumor, and can be said to be a region which is highly suspected that a lesion part is positioned, and is a target for the biopsy.

The needle detection unit 36 detects the tissue sampling needle pierced into the breast of the subject on the basis of the ultrasound image. The needle detection unit 36 can detect the tissue sampling needle shown in the ultrasound image by using, for example, an image recognition method including pattern matching and extraction of the feature amount, or a deep learning method.

Figure 5:
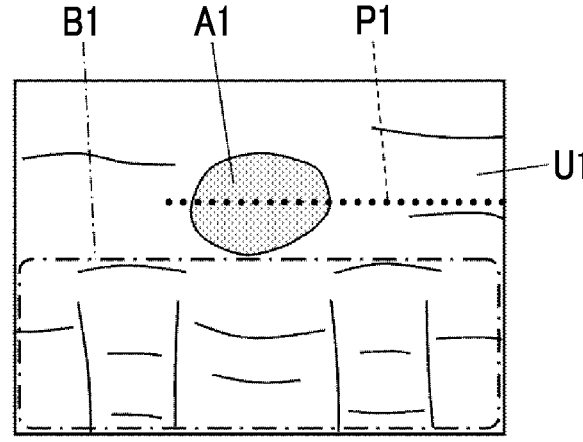
FIG. 5 is a diagram illustrating an example of a recommended path that passes through a sampling target region and is parallel to the pectoralis major muscle in the first embodiment of the present invention.

The recommended path calculation unit 37 calculates a recommended path of the tissue sampling needle that passes through the sampling target region extracted by the region extraction unit 55. For example, as illustrated in FIG. 5, the recommended path calculation unit 37 can detect a pectoralis major muscle region B1 in an ultrasound image U1 by performing an image analysis on the ultrasound image U1, and further calculate a recommended path P1 that passes through a sampling target region A1 and is parallel to the pectoralis major muscle region B1. Note that the recommended path calculation unit 37 can use an image recognition method such as pattern matching or extraction of a feature amount, a deep learning method, or the like in a case of detecting the pectoralis major muscle region B1.

Further, in a case where the tissue sampling needle is detected by the needle detection unit 36, the recommended path calculation unit 37 can correct the recommended path P1 on the basis of the positional relationship between the detected tissue sampling needle and the sampling target region detected by the sampling target region detection unit 35. For example, as illustrated in FIG. 6, in a case where a tissue sampling needle N1 advancing toward the sampling target region A1 is detected by the needle detection unit 36, the recommended path calculation unit 37 can set a straight line passing through both the distal end of the detected tissue sampling needle N1 and the location with the highest malignancy in the sampling target region A1, as the recommended path P1. The examiner pierces the breast of the subject with the tissue sampling needle N1 along the recommended path P1, and thereby the distal end of the tissue sampling needle N1 can pass through the sampling target region A1 as illustrated in FIG. 7.

The needle passage determination unit 38 determines whether or not the tissue sampling needle N1 pierced into the breast of the subject has passed through the sampling target region A1. For example, the needle passage determination unit 38 recognizes a positional relationship, on the ultrasound image U1, between the sampling target region A1 detected by the sampling target region detection unit 35 and the tissue sampling needle N1 detected by the needle detection unit 36, and can determine that the tissue sampling needle N1 has passed through the sampling target region A1 in a case where it is recognized that the tissue sampling needle N1 passes through the sampling target region A1 and the distal end of the tissue sampling needle N1 has reached the outside of the sampling target region A1.

Further, the needle passage determination unit 38 can display the determination result on the monitor 33 in a case where it is determined that the tissue sampling needle N1 has passed through the sampling target region A1.

The processor 42 having the image generation unit 31, the display controller 32, the sampling target region detection unit 35, the needle detection unit 36, the recommended path calculation unit 37, the needle passage determination unit 38, and the main body controller 40 is configured by a central processing unit (CPU) and a control program for causing the CPU to execute various kinds of processing, but the processor 42 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 31, the display controller 32, the sampling target region detection unit 35, the needle detection unit 36, the recommended path calculation unit 37, the needle passage determination unit 38, and the main body controller 40 of the processor 42 can also be configured by being integrated partially or entirely into one CPU or the like.

Next, the operation of the ultrasound diagnostic apparatus 1 according to the first embodiment of the present invention will be described using the flowchart illustrated in FIG. 8.

First, in Step S1, the examiner performs an input operation via the input device 41 so that an instruction to perform a biopsy on the subject is input. As a result, the main body controller 40 activates a biopsy mode according to the instruction from the examiner, and the biopsy for the subject is started. Here, the biopsy mode is a mode in which the ultrasound diagnostic apparatus 1 performs characteristic operations of the present invention, as illustrated in Steps S2 to S12 after Step S1.

Next, in Step S2, the examiner brings the ultrasound probe 2 into contact with the breast of the subject, and the ultrasound image U1 is acquired in this state. In a case where the ultrasound image U1 is acquired, the transmission and reception circuit 22 performs so-called reception focusing processing under the control of the main body controller 40 to generate sound ray signals. The sound ray signals generated by the transmission and reception circuit 22 are sent to the image generation unit 31. The image generation unit 31 generates the ultrasound image U1 using the sound ray signals sent from the transmission and reception circuit 22. The ultrasound image U1 acquired in this manner is sent to the display controller 32 and the image memory 34. The ultrasound image U1 sent to the display controller 32 is displayed on the monitor 33 after being subjected to predetermined processing. Further, the ultrasound image U1 sent to the image memory 34 is stored in the image memory 34.

The examiner pierces the breast of the subject with the tissue sampling needle N1 while observing the ultrasound image U1 of the inside of the breast of the subject acquired in this manner.

Next, in Step S3, the sampling target region detection unit 35 detects the sampling target region A1 in which the tissue is sampled from the subject by the tissue sampling needle N1, on the basis of the ultrasound image U1 that is acquired in Step S2 and is stored in the image memory 34.

In this case, the malignancy determination unit 54 of the sampling target region detection unit 35 recognizes a region suspected to be a lesion part such as a tumor on the ultrasound image U1, and sets a region of interest including the recognized region. The malignancy determination unit 54 determines the malignancy in the set region of interest in units of pixels by using an image analysis method, a machine learning method, or a deep learning method, for example.

Further, the region extraction unit 55 of the sampling target region detection unit 35 extracts a region including a set of pixels of which the value of the malignancy determined by the malignancy determination unit 54 is equal to or greater than the predetermined threshold value, as the sampling target region A1. In this case, the malignancy determination unit 54 can further display the malignancy determined for each pixel in the region of interest, as a heat map on the monitor 33. As a result, the examiner can easily understand the region with a high possibility that malignant tissues, that is, tissues to be sampled in the biopsy are distributed.

In subsequent Step S4, the recommended path calculation unit 37 calculates the recommended path P1 of the tissue sampling needle N1 passing through the sampling target region A1 detected in Step S3. In this case, for example, as illustrated in FIG. 5, the recommended path calculation unit 37 can detect a pectoralis major muscle region B1 in an ultrasound image U1 by performing an image analysis on the ultrasound image U1, and further calculate a recommended path P1 that passes through a sampling target region A1 and is parallel to the pectoralis major muscle region B1. The examiner causes the distal end of the tissue sampling needle N1 to advance along the calculated recommended path P1 so as to allow that the distal end of the tissue sampling needle N1 can safely advance so as to pass through the sampling target region A1 and not to reach the pectoralis major muscle.

In Step S5, the ultrasound image U1 that is acquired is Step S2 and is displayed on the monitor 33, and the recommended path P1 calculated in Step S3 are displayed on the monitor 33. In this case, the recommended path calculation unit 37 displays the recommended path P1 on the monitor 33 such that the recommended path P1 is superimposed on the ultrasound image U1.

In Step S6, the needle detection unit 36 performs an image analysis on the ultrasound image U1 acquired in Step S2 to perform processing of detecting the tissue sampling needle N1 pierced into the breast of the subject. In a case where the tissue sampling needle N1 is not detected here, the processing returns to Step S1.

In this manner, the processing of Steps S2 to S6 is repeated until the tissue sampling needle N1 is detected in Step S6. In the second and subsequent Step S3, the sampling target region detection unit 35 can set the sampling target region A1 on the ultrasound image U1 by aligning the sampling target region A1 detected in the first Step S3 on an ultrasound image U1 newly acquired in Step S2, by using, for example, a so-called block matching method or a so-called gradient method. Further, in the second and subsequent Step S4, the recommended path calculation unit 37 can set the recommended path P1 on the ultrasound image U1 by aligning the recommended path P1 calculated in the first Step S4 on a ultrasound image U1 newly acquired in Step S2, by using, for example, a block matching method or a gradient method.

In a case where the tissue sampling needle N1 is detected in Step S6, the processing proceeds to Step S7.

In Step S7, the recommended path calculation unit 37 corrects the recommended path P1 calculated in Step S3 on the basis of the positional relationship between the sampling target region A1 detected in Step S2 and the tissue sampling needle N1 detected in Step S5. In this case, as illustrated in FIG. 6, the recommended path calculation unit 37 can set a straight line passing through both the distal end of the detected tissue sampling needle N1 and the location with the highest malignancy in the sampling target region A1, as the recommended path P1.

In Step S8, similarly to Step S5, the ultrasound image U1 acquired in Step S1 and the recommended path P1 corrected in Step S7 are displayed on the monitor 33 in a superimposed manner. The examiner pierces the breast of the subject with the tissue sampling needle N1 along the recommended path P1 displayed on the monitor 33, and thereby the distal end of the tissue sampling needle N1 can pass through the sampling target region A1 as illustrated in FIG. 7.

In Step S9, the needle passage determination unit 38 determines whether or not the tissue sampling needle N1 pierced into the breast of the subject has passed through the sampling target region A1 detected in Step S2. In this case, in a case where it is recognized, for example, that the tissue sampling needle N1 detected in Step S5 passes through the sampling target region A1 detected in Step S2 and the distal end of the tissue sampling needle N1 has reached the outside of the sampling target region A1 on the ultrasound image U1, the needle passage determination unit 38 can determine that the tissue sampling needle N1 has passed through the sampling target region A1.

In a case where it is determined in Step S9 that the tissue sampling needle N1 has not passed through the sampling target region A1, the processing proceeds to Step S10. In Step S10, similarly to Step S2, a new ultrasound image U1 representing a cross-cross section of the breast of the subject is acquired. In this case, the sampling target region detection unit 35 can set the sampling target region A1 detected in Step S3 on the ultrasound image U1 acquired in Step S10 by aligning the sampling target region A1 detected in Step S3 on the ultrasound image U1 acquired in Step S10, by using, for example, a block matching method or a gradient method. Further, the recommended path calculation unit 37 can set the recommended path P1 corrected in Step S7 on the ultrasound image U1 acquired in Step S10 by aligning the recommended path P1 corrected in Step S7 on the ultrasound image U1 acquired in Step S10, by using, for example, a block matching method or a gradient method.

In Step S11, similarly to Step S5 and Step S8, the recommended path P1 corrected in Step S7 and the ultrasound image U1 acquired in Step S10 are displayed on the monitor 33 in a superimposed manner.

In Step S12, the needle detection unit 36 detects the tissue sampling needle N1 from the ultrasound image U1 acquired in Step S10. In this case, the needle detection unit 36 can detect the tissue sampling needle N1 by tracing the tissue sampling needle N1 detected in Step S6 on the ultrasound image U1 acquired in Step S10, by using, for example, a block matching method or a gradient method.

In this manner, the processing of Steps S9 to S12 is repeated until it is determined in Step S9 that the tissue sampling needle N1 has passed through the sampling target region A1.

In a case where it is determined in Step S9 that the tissue sampling needle N1 has passed through the sampling target region A1, the operation of the ultrasound diagnostic apparatus 1 according to the flowchart of FIG. 8 is ended. Here, in a case where it is determined in Step S9 that the tissue sampling needle N1 has passed through the sampling target region A1, the needle passage determination unit 38 can notify the examiner that the tissue sampling needle N1 has passed through the sampling target region A1 by, for example, displaying a message on the monitor 33 or the like. The examiner can smoothly proceed with the biopsy while understanding that the tissue sampling needle N1 has passed through the sampling target region A1 and thus the tissue in the sampling target region A1 has been sampled by the tissue sampling needle N1.

As described above, with the ultrasound diagnostic apparatus 1 according to the first embodiment of the present invention, the sampling target region A1 is detected on the ultrasound image U1, the recommended path P1 of the tissue sampling needle N1 passing through the sampling target region A1 is calculated, the recommended path P1 is displayed to be superimposed on the ultrasound image U1, the tissue sampling needle N1 is detected on the ultrasound image U1, and it is determined whether or not the tissue sampling needle N1 has passed through the sampling target region A1. Therefore, the examiner can allow the distal end of the tissue sampling needle N1 to accurately advance to pass through the sampling target region A1, and the biopsy can be reliably performed in a short time even by an unskilled examiner.

The description has been made in which in a case where the ultrasound image U1 is acquired in Step S10, the sampling target region A1 detected in Step S3 and the recommended path P1 corrected in Step S7 are aligned on the ultrasound image U1 acquired in Step S10, so that the sampling target region A1 and the recommended path P1 are set on the ultrasound image U1 acquired in Step S10. However, the sampling target region A1 and the recommended path P1 can be set on the ultrasound image U1 by performing the same processing as Step S3 and Step S4 after the ultrasound image U1 is acquired in Step S10.

Further, the description has been made in which the transmission and reception circuit 22 is included in the ultrasound probe 2, but the transmission and reception circuit 22 can be included in the apparatus main body 3 instead of being included in the ultrasound probe 2.

Further, the description has been made in which the image generation unit 31 is included in the apparatus main body 3, but the image generation unit 31 can be included in the ultrasound probe 2 instead of being included in the apparatus main body 3.

Further, the ultrasound probe 2 and the apparatus main body 3 can be connected to each other by so-called wired communication using a cable, or can also be connected to each other by so-called wireless communication.

Further, the description has been made in which the needle passage determination unit 38 determines that the tissue sampling needle N1 has passed through the sampling target region A1 by recognizing that the tissue sampling needle N1 detected by the needle detection unit 36 passes through the sampling target region A1 and the distal end of the tissue sampling needle N1 has reached the outside of the sampling target region A1 on the ultrasound image U1, but the determination method is not particularly limited. In a case where the length of the tissue sampling needle N1 having passed through the inside of the sampling target region A1 is equal to or greater than a predetermined ratio with respect to the length of the recommended path P1 in the sampling target region A1, the needle passage determination unit 38 can determine that the tissue sampling needle N1 has passed through the sampling target region A1. As a result, it can be determined that the tissue sampling needle N1 has passed through the sampling target region A1 along the recommended path P1.

The description has been made in which the region extraction unit 55 of the sampling target region detection unit 35 extracts a region in which the malignancy determined by the malignancy determination unit 54 is equal to or greater than the predetermined threshold value, as the sampling target region A1, but the region extraction unit 55 can calculate the threshold value of the malignancy on the basis of the malignancy determined by the malignancy determination unit 54. The region extraction unit 55 can calculate the threshold value for the value of the malignancy by, for example, multiplying the maximum value of the determined malignancy in the region of interest by a predetermined ratio. As a result, for example, even in a case where only a relatively low value of the malignancy is obtained, the sampling target region A1 can be reliably set.

Further, the sampling target region detection unit 35 can calculate the area of the detected sampling target region A1, and display the calculated value of the area on the monitor 33. The examiner can easily understand the size of the sampling target region A1 by checking the value of the area of the sampling target region A1 displayed on the monitor 33.

Further, it is considered that the distribution of the malignancy in the sampling target region A1 is changed in a case where a part of the tumor or the like in the breast of the subject corresponding to the sampling target region A1 is sampled by the tissue sampling needle N1. Therefore, the sampling target region detection unit 35 can detect the sampling target region A1 on the basis of the ultrasound image U1 generated by the image generation unit 31 before the piercing of the tissue sampling needle N1, and detect again the sampling target region A1 on the basis of the ultrasound image U1 generated by the image generation unit 31 after the tissue sampling needle N1 retreats from the sampling target region A1. Whether or not the tissue sampling needle N1 has retreated from the sampling target region A1 can be determined by the needle passage determination unit 38.

In this manner, since the sampling target region A1 in which the current distribution of the malignancy in the sampling target region A1 is reflected is detected, the examiner can accurately understand the region to be subjected to the biopsy on the ultrasound image U1.

In this case, the sampling target region detection unit 35 can calculate both the area of the sampling target region A1 in the ultrasound image U1 before the piercing of the tissue sampling needle N1, and the area of the sampling target region A1 in the ultrasound image U1 after the tissue sampling needle N1 retreats from the sampling target region A1, and display the values of both the areas on the monitor 33. The examiner can easily understand how much tissue is sampled by comparing the value of the area of the sampling target region A1 before the piercing of the tissue sampling needle N1 with the value of the area of the sampling target region A1 after the tissue sampling needle N1 retreats.

Further, in a case where the transducer array 21 of the ultrasound probe 2 has a plurality of ultrasonic transducers arranged two-dimensionally, the image acquisition unit F can acquire a three-dimensional ultrasound image U1 by three-dimensionally scanning the inside of the subject.

In this case, the sampling target region detection unit 35 can detect the three-dimensional sampling target region A1 on the basis of the three-dimensional ultrasound image U1, calculate the volume of the detected sampling target region A1, and display the value of the calculated volume on the monitor 33. The examiner can easily understand the size of the sampling target region A1 by checking the value of the volume of the sampling target region A1 displayed on the monitor 33.

Further, even in a case where the three-dimensional ultrasound image U1 is acquired, the sampling target region detection unit 35 can detect the sampling target region A1 on the basis of the ultrasound image U1 generated by the image generation unit 31 before the piercing of the tissue sampling needle N1, and detect again the sampling target region A1 on the basis of the ultrasound image U1 generated by the image generation unit 31 after the tissue sampling needle N1 retreats from the sampling target region A1. As a result, since the sampling target region A1 in which the current distribution of the malignancy is reflected is detected, the examiner can accurately understand the region to be subjected to the biopsy on the ultrasound image U1.

Further, the description has been made in which the malignancy determination unit 54 recognizes a region suspected to be a lesion part such as a tumor, but the examiner can manually set a region suspected to be a lesion part via the input device 41 by checking the ultrasound image U1. In this case, the malignancy determination unit 54 can set a region of interest including the region suspected to be a lesion part set by the examiner, on the ultrasound image U1, and determine the malignancy in each portion in the region of interest.

Second Embodiment

In a case of piercing the breast of the subject with the tissue sampling needle N1, in general, the distal end of the tissue sampling needle N1 is carefully pierced so as not to enter the pectoralis major muscle. The ultrasound diagnostic apparatus 1 can also issue a warning in a case where the tissue sampling needle N1 is predicted to advance toward the pectoralis major muscle.

FIG. 9 illustrates a configuration of an ultrasound diagnostic apparatus 1A according to a second embodiment. The ultrasound diagnostic apparatus 1A is obtained by comprising an apparatus main body 3A instead of the apparatus main body 3 in the ultrasound diagnostic apparatus 1 of the first embodiment illustrated in FIG. 1. The apparatus main body 3A in the second embodiment is obtained by adding a warning unit 61 to the apparatus main body 3 in the first embodiment, and comprising a main body controller 40A instead of the main body controller 40.

In the apparatus main body 3A, the sampling target region detection unit 35 and the needle detection unit 36 are connected to the warning unit 61. Further, the warning unit 61 is connected to the display controller 32 and the main body controller 40A. Further, the image generation unit 31, the display controller 32, the sampling target region detection unit 35, the needle detection unit 36, the recommended path calculation unit 37, the needle passage determination unit 38, the main body controller 40A, and the warning unit 61 constitute a processor 42A for the apparatus main body 3A.

The sampling target region detection unit 35 detects the sampling target region A1 and the pectoralis major muscle region B1 in the ultrasound image U1 by performing an image analysis on the ultrasound image U1 stored in the image memory 34.

The warning unit 61 predicts whether or not the tissue sampling needle N1 advances toward the pectoralis major muscle on the basis of the pectoralis major muscle region B1 detected by the sampling target region detection unit 35 and the tissue sampling needle N1 detected on the ultrasound image U1 by the needle detection unit 36, and issues a warning in a case where it is predicted that the tissue sampling needle N1 advances toward the pectoralis major muscle.

Here, in a case where the sampling target region A1 is positioned at a shallow portion in the subject, since there is a sufficient distance between the sampling target region A1 and the pectoralis major muscle region B1, a risk of the tissue sampling needle N1 entering the pectoralis major muscle is relatively low even in a case where the distal end of the tissue sampling needle N1 faces the pectoralis major muscle region B1. However in a case where the sampling target region A1 is positioned at a deep portion in the subject, that is, in a case where the sampling target region A1 is positioned near the pectoralis major muscle region B1, and in a case where the distal end of the tissue sampling needle N1 faces the pectoralis major muscle region B1, a risk of the tissue sampling needle N1 entering the pectoralis major muscle is relatively high when the tissue sampling needle N1 passes through the sampling target region A1.

Thus, for example, the warning unit 61 can recognize the positional relationship between pectoralis major muscle region B1 and the sampling target region A1 detected by the sampling target region detection unit 35, and the position and direction of the tissue sampling needle N1 detected by the needle detection unit 36, and predict that the tissue sampling needle N1 advances toward the pectoralis major muscle in a case where an extension line L1 extending from the distal end of the tissue sampling needle N1 along the direction of the tissue sampling needle N1 intersects the pectoralis major muscle region B1 and the distance between the sampling target region A1 and the pectoralis major muscle region B1 is equal to or greater than a certain value, as illustrated in FIG. 10. As the distance between the sampling target region A1 and the pectoralis major muscle region B1, the warning unit 61 can evaluate, for example, a distance between the sampling target region A1 and the pectoralis major muscle region B1 in a depth direction of the ultrasound image U1, and also evaluate a distance between the sampling target region A1 and the pectoralis major muscle region B1 along the extension line L1.

Although not illustrated, the warning unit 61 can issue a warning by displaying a message such as "danger!" on the monitor 33.

As described above, with the ultrasound diagnostic apparatus 1A according to the second embodiment, since the warning unit 61 issues a warning in a case where it is predicted that the tissue sampling needle N1 detected by the needle detection unit 36 advances toward the pectoralis major muscle, the examiner can safely pierce the subject with the tissue sampling needle N1 so that the distal end of the tissue sampling needle N1 does not enter the pectoralis major muscle, by checking the warning.

Third Embodiment

In order to check the location where the biopsy has been performed by the tissue sampling needle N1 after the examination, it is also possible to store information regarding a piercing final point reached by the tissue sampling needle N1.

FIG. 11 illustrates a configuration of an ultrasound diagnostic apparatus 1B according to a third embodiment. The ultrasound diagnostic apparatus 1B is obtained by comprising an apparatus main body 3B instead of the apparatus main body 3 in the ultrasound diagnostic apparatus 1 of the first embodiment illustrated in FIG. 1. The apparatus main body 3B in the third embodiment is obtained by adding a final point reach determination unit 62 and an examination result memory 63 to the apparatus main body 3 in the first embodiment, and comprising a main body controller 40B instead of the main body controller 40.

In the apparatus main body 3B, the final point reach determination unit 62 is connected to the needle detection unit 36. Further, the examination result memory 63 is connected to the final point reach determination unit 62. The final point reach determination unit 62 and the examination result memory 63 are connected to the main body controller 40B. The examination result memory 63 is also connected to the image memory 34. Further, the image generation unit 31, the display controller 32, the sampling target region detection unit 35, the needle detection unit 36, the recommended path calculation unit 37, the needle passage determination unit 38, the main body controller 40B, and the final point reach determination unit 62 constitute a processor 42B for the apparatus main body 3B.

The final point reach determination unit 62 determines whether or not the tissue sampling needle N1 has reached the piercing final point on the basis of the detection of the tissue sampling needle N1 by the needle detection unit 36. For example, as illustrated in FIG. 12, in a case where the advance direction of the distal end of the tissue sampling needle N1 that has advanced toward the deep portion from the body surface of the subject is changed in the opposite direction, that is, in a direction from the deep portion of the subject toward the body surface, the final point reach determination unit 62 determines that the tissue sampling needle N1 has reached a piercing final point T by determining a point where the advance direction the distal end of the tissue sampling needle N1 is changed in the opposite direction, as the final point T. The final point reach determination unit 62 sends the determination result to the main body controller 40B.

Further, the final point reach determination unit 62 can acquire coordinates of the tissue sampling needle N1 on the ultrasound image U1 at the time of determining that the tissue sampling needle N1 has reached the final point T, and send the coordinates to the examination result memory 63. Here, the coordinates of the tissue sampling needle N1 are a set of coordinates representing the overall position of the tissue sampling needle N1.

Further, the final point reach determination unit 62 can extract the ultrasound image of the tissue sampling needle N1 at the time of determining that the tissue sampling needle N1 has reached the final point T, and send the extracted ultrasound image of the tissue sampling needle N1 to the examination result memory 63.

Under the control of the main body controller 40B, the examination result memory 63 stores various ultrasound image U1 and data. Specifically, the examination result memory 63 stores the ultrasound image U1 acquired by the image acquisition unit F before the tissue sampling needle N1 passes through the sampling target region A1. The examination result memory 63 further stores the ultrasound image U1, which is acquired by the image acquisition unit F, the coordinates of the tissue sampling needle N1 detected by the needle detection unit 36, or the ultrasound image of the tissue sampling needle N1 detected by the needle detection unit 36, which are acquired or detected at the time when the final point reach determination unit 62 determines that the tissue sampling needle N1 has reached the final point T. The examination result memory 63 further stores the ultrasound image U1 including the sampling target region A1 after the tissue sampling needle N1 is pulled out from the breast of the subject.

The ultrasound image U1 acquired by the image acquisition unit F before the tissue sampling needle N1 passes through the sampling target region A1 is stored in order for the examiner or the like to check the region suspected to be a lesion part before the biopsy. Further, the ultrasound image U1 acquired by the image acquisition unit F and the coordinates of the tissue sampling needle N1 or the ultrasound image of the tissue sampling needle N1 at the time when the final point reach determination unit 62 determines that the tissue sampling needle N1 has reached the final point T are stored in order for the examiner or the like to check the state of the tissue sampling needle N1 during the biopsy. The ultrasound image U1 including the sampling target region A1 after the tissue sampling needle N1 is pulled out from the breast of the subject is stored in order for the examiner or the like to check the region subject to be a lesion part after the biopsy is performed.

In a case where the coordinates of the tissue sampling needle N1 are stored, the examination result memory 63 can store, for example, the coordinates of the tissue sampling needle N1 in a so-called Digital Imaging and Communications in Medicine (DICOM) standard format such as gray-scale softcopy presentation state (GSPS). For example, an identifier (ID) of the ultrasound image U1 which is acquired by the image acquisition unit F before the tissue sampling needle N1 passes through the sampling target region A1 and is stored in the examination result memory 63 is included in the GSPS. In a case where the ultrasound image U1 corresponding to the ID is displayed on, for example, an external so-called picture archiving and communication system (PACS) viewer, an image corresponding to the tissue sampling needle N1 can be depicted in a region corresponding to the coordinates of the tissue sampling needle N1, on the ultrasound image U1.

In this case, since the coordinates of the tissue sampling needle N1 are only stored as the information of the tissue sampling needle N1, the information amount to be stored in the examination result memory 63 can be reduced and the storage capacity of the examination result memory 63 can be saved as compared with a case where the ultrasound image U1 at the time when the tissue sampling needle N1 has reached the final point T is stored.

In a case where the ultrasound image of the tissue sampling needle N1 is stored, the examination result memory 63 can store a 1-bit black and white image in a DICOM so-called "overlay" tag for the ultrasound image U1 acquired by the image acquisition unit F before the tissue sampling needle N1 passes through the sampling target region A1, for example. In this case, in a case where the ultrasound image U1 acquired before the tissue sampling needle N1 passes through the sampling target region A1 is displayed on, for example, an external PACS viewer, the operator of the viewer can superimpose and display the image of the tissue sampling needle N1 stored in the examination result memory 63 on the ultrasound image U1, and display only the ultrasound image U1 by erasing the image of the tissue sampling needle N1 that has been superimposed and displayed on the ultrasound image U1 via the input operation. Therefore, it is possible for the operator of the viewer to easily check the result of the biopsy.

Further, in this case, since the 1-bit image of the tissue sampling needle N1 is only stored as the information of the tissue sampling needle N1, the information amount to be stored in the examination result memory 63 can be reduced and the storage capacity of the examination result memory 63 can be saved as compared with a case where the entire ultrasound image U1 at the time when the tissue sampling needle N1 has reached the final point T is stored.

As described above, with the ultrasound diagnostic apparatus 1B according to the third embodiment, it is automatically determined that the tissue sampling needle N1 has reached the piercing final point T. Further, the examination result memory 63 automatically stores the ultrasound image U1 acquired by the image acquisition unit F before the tissue sampling needle N1 passes through the sampling target region A1 and the ultrasound image U1, which is acquired by the image acquisition unit F, the coordinates of the tissue sampling needle N1 detected by the needle detection unit 36, or the ultrasound image of the tissue sampling needle N1 detected by the needle detection unit 36, which are acquired or detected at the time when the final point reach determination unit 62 determines that the tissue sampling needle N1 has reached the final point T. Therefore, an appropriate examination result can be reliably stored while an examiner performs a biopsy smoothly without interrupting the biopsy. Further, the storage capacity of the examination result memory 63 can also be saved. For example, the operator viewing the ultrasound image U1 stored in the examination result memory 63 with the external PACS viewer can freely display or delete the image of the tissue sampling needle N1 on the ultrasound image U1, and therefore can easily check the result of the biopsy.

When it is determined that the tissue sampling needle N1 has reached the piercing final point T, in a case where the needle passage determination unit 38 determines that the tissue sampling needle N1 has not passed through the sampling target region A1, the needle detection unit 36 detects an actual path G1 of the tissue sampling needle N1, and the recommended path calculation unit 37 can set a path obtained by the parallel translation of the actual path G1 of the tissue sampling needle N1 in any one of upward, downward, left, and right directions on the ultrasound image U1 to pass through the sampling target region A1, as a new recommended path P2. The recommended path calculation unit 37 can set the new recommended path P2 by drawing a plurality of perpendicular lines from the actual path G1 of the tissue sampling needle N1 to the linear recommended path P1 and performing the parallel translation of the actual path G1 in any one of upward, downward, left, and right directions so that the sum of the lengths of the plurality of perpendicular lines in the sampling target region A1 is minimized. FIG. 13 illustrates an example of the deflected path G1 that has deviated from the sampling target region A1 due to the deflection or the like of the tissue sampling needle N1 in the subject, and an example of the new recommended path P2 set by the parallel translation of the deflected path G1 in the upward direction.

In a case where the new recommended path P2 is set in this manner, the examiner can retreat the tissue sampling needle N1 to the shallow portion, that is, the body surface side of the subject once, and pierce the breast of the subject with the tissue sampling needle N1 along the newly set recommended path P2, and thereby the distal end of the tissue sampling needle N1 can advance to pass through the sampling target region A1.

Further, the description has been made in which the form of the third embodiment is applied to the form of the first embodiment, but the form of the third embodiment can be appropriately combined with the form of the second embodiment.

Fourth Embodiment

The tissue sampling needle N1 pierced into the breast of the subject can be deflected by the tissues in the breast of the subject. The ultrasound diagnostic apparatus 1 can display a deflection occurrence region in an emphasized manner such that the examiner can more accurately perform the biopsy by easily understanding the deflection occurrence region in the breast of the subject where the deflection of the tissue sampling needle N1 has occurred.

FIG. 14 illustrates a configuration of an ultrasound diagnostic apparatus 1C according to a fourth embodiment. The ultrasound diagnostic apparatus 1C is obtained by comprising an apparatus main body 3C instead of the apparatus main body 3 in the ultrasound diagnostic apparatus 1 of the first embodiment illustrated in FIG. 1.

The apparatus main body 3C in the fourth embodiment is obtained by adding a deflection detection unit 64 and an emphasizing unit 65 to the apparatus main body 3 in the first embodiment, and comprising a main body controller 40C instead of the main body controller 40. In the apparatus main body 3C, the needle detection unit 36 is connected to the deflection detection unit 64. The emphasizing unit 65 is connected to the image generation unit 31 and the deflection detection unit 64. The emphasizing unit 65 is connected to the display controller 32. The deflection detection unit 64 and the emphasizing unit 65 are connected to the main body controller 40C. Further, the image generation unit 31, the display controller 32, the sampling target region detection unit 35, the needle detection unit 36, the recommended path calculation unit 37, the needle passage determination unit 38, the main body controller 40C, the deflection detection unit 64, and the emphasizing unit 65 constitute a processor 42C for the apparatus main body 3C.

For example, as illustrated in FIG. 15, the deflection detection unit 64 detects the path G1 through which the tissue sampling needle N1 has passed in the ultrasound image U1 on the basis of the detection of the tissue sampling needle N1 by the needle detection unit 36, and detects the deflection occurring in the path G1. In this case, the deflection detection unit 64 can detect the deflection occurring in the path G1 through which the tissue sampling needle N1 has passed by using, for example, an image recognition method including pattern matching and extraction of the feature amount, or a deep learning method.

The emphasizing unit 65 detects a brightness value of the ultrasound image U1 for the position where the deflection is detected by the deflection detection unit 64, emphasizes a continuous region having a brightness value within a predetermined range for the detected brightness value, as a deflection occurrence region E1, and displays the deflection occurrence region E1 on the monitor 33.

Here, the brightness value within the predetermined range for the detected brightness value refers to a brightness value within a certain range including the detected brightness value, and can be set to a brightness value within a range that is equal to or higher than a brightness value lower than the detected brightness value by a predetermined value and is equal to or lower than a brightness value higher than the detected brightness value by a predetermined value. That is, the lower limit value of the brightness value within the predetermined range for the detected brightness value is a value obtained by subtracting the determined value from the detected brightness value. The upper limit value of the brightness value within the predetermined range for the detected brightness value is a value obtained by adding the determined value to the detected brightness value.

Further, the emphasizing unit 65 can emphasize and display the deflection occurrence region E1 on the monitor 33 by displaying the deflection occurrence region E1 in a display mode different from the surroundings, such as by displaying a contour line C1 of the deflection occurrence region E1 indicated by the dotted line in FIG. 15 and imparting a color different from the surroundings to the deflection occurrence region E1.

As described above, with the ultrasound diagnostic apparatus 1C according to the fourth embodiment, the deflection occurring in the path G1 through which the tissue sampling needle N1 has passed is detected, and the continuous region having a brightness value within a predetermined range for the brightness value of the ultrasound image U1 for the position where the deflection is detected is emphasized and displayed as the deflection occurrence region E1 on the monitor 33. Therefore, the examiner can easily understand the position of the deflection occurrence region E1, more accurately cause the tissue sampling needle N1 to advance up to the sampling target region A1, and reliably perform the biopsy.

In a case where the deflection has occurred in the path G1 through which the tissue sampling needle N1 has passed, the advance direction of the tissue sampling needle N1 in the deflection occurrence region E1 may deviate from the advance direction desired by the examiner, and as a result, the path G1 of the tissue sampling needle N1 may deviate from the sampling target region A1. Thus, the recommended path calculation unit 37 can calculate the recommended path P1 by taking into consideration the position of the deflection occurrence region E1 detected by the deflection detection unit 64, for example.

In this case, in a case where the tissue sampling needle N1 advances into the deflection occurrence region E1, the recommended path calculation unit 37 can calculate a recommended path P3 deflected in the deflection occurrence region E1 on the assumption that the tissue sampling needle N1 advances along a deflected path similar to the deflection of the actual path G1 detected by the deflection detection unit 64. In this case, the recommended path calculation unit 37 can calculate a deflection amount that the path G1 is deflected for a certain number of pixels in the ultrasound image U1, and calculate a deflection amount of the new recommended path P3 in the deflection occurrence region E1 according to the number of pixels of a portion where the linear recommended path P1 before the deflection is considered and the deflection occurrence region E1 overlap, on the basis of the calculated deflection amount.

As a result, the examiner can perform piercing with the tissue sampling needle N1 while checking the recommended path P3 in which the deflection of the tissue sampling needle N1 in the deflection occurrence region E1 is considered, and therefore can reliably perform the biopsy even in a case where the path G1 of the tissue sampling needle N1 is deflected.

Further, the description has been made in which the form of the fourth embodiment is applied to the first embodiment, but the form of the fourth embodiment can be appropriately combined with the forms of the second embodiment and the third embodiment.

EXPLANATION OF REFERENCES 1, 1A, 1B, 1C: ultrasound diagnostic apparatus
2: ultrasound probe
3, 3A, 3B, 3C: apparatus main body
21: transducer array
22: transmission and reception circuit
23: pulser
24: amplification unit
25: AD conversion unit
26: beam former
31: image generation unit
32: display controller
33: monitor
35: sampling target region detection unit
36: needle detection unit
37: recommended path calculation unit
38: needle passage determination unit
40, 40A, 40B, 40C: main body controller
41: input device
42, 42A, 42B, 42C: processor
51: signal processing unit
52: DSC
53: image processing unit
54: malignancy determination unit
55: region extraction unit
61: warning unit
62: final point reach determination unit
63: examination result memory
64: deflection detection unit
65: emphasizing unit
A1: sampling target region
B1: pectoralis major muscle region
C1: contour line
E1: deflection occurrence region
F: image acquisition unit
G1: path
L1: extension line
N1: tissue sampling needle
P1, P2: recommended path
T: final point
U1: ultrasound image

What is claimed is:

1. An ultrasound diagnostic apparatus comprising:
a monitor; and
a processor configured to:
acquire a plurality of ultrasound images in which a breast of a subject is captured;
determine a malignancy value in each of a plurality of portions in a region of interest of the breast of the subject in the plurality of ultrasound images by analyzing the plurality of ultrasound images;
calculate a malignancy threshold value by multiplying a predetermined ratio to a maximum value of the malignancy values;

detect a region in which the malignancy value is greater than or equal to the malignancy threshold value as a sampling target region in which a tissue is sampled from the subject by a tissue sampling needle based on each of the plurality of ultrasound images;
calculate a recommended path of the tissue sampling needle passing through the sampling target region;
display the plurality of ultrasound images sequentially on the monitor;
display the recommended path superimposed on each of the plurality of ultrasound images on the monitor;
detect a location of a distal end of the tissue sampling needle in at least one of the plurality of ultrasound images;
based on detecting the location of the distal end of the tissue sampling needle, make a determination that the distal end of the tissue sampling needle enters the sampling target region from an entry point on a contour of the sampling target region and then exits the sampling target region from an exit point on the contour different from the entry point; and
after the determination, notify an examiner that the tissue sampling needle has passed through the sampling target region.

2. The ultrasound diagnostic apparatus according to claim 1,
wherein the processor is configured to display a determination result of the malignancy value in each of the plurality of portions in the region of interest on the monitor.

3. The ultrasound diagnostic apparatus according to claim 2,
wherein the processor is configured to display a heat map of the determined malignancy values as the determination result on the monitor.

4. The ultrasound diagnostic apparatus according to claim 1,
wherein the processor is configured to
detect pectoralis major muscle of the subject based on each of the plurality of ultrasound images, and
calculate a path that passes through the sampling target region and is parallel to the pectoralis major muscle, as the recommended path until the tissue sampling needle is detected.

5. The ultrasound diagnostic apparatus according to claim 2,
wherein the processor is configured to
detect pectoralis major muscle of the subject based on each of the plurality of ultrasound images, and
calculate a path that passes through the sampling target region and is parallel to the pectoralis major muscle, as the recommended path until the tissue sampling needle is detected.

6. The ultrasound diagnostic apparatus according to claim 3,
wherein the processor is configured to
detect pectoralis major muscle of the subject based on each of the plurality of ultrasound images, and
calculate a path that passes through the sampling target region and is parallel to the pectoralis major muscle, as the recommended path until the tissue sampling needle is detected.

7. The ultrasound diagnostic apparatus according to claim 1,
wherein in a case where a length of the tissue sampling needle, which is detected, having passed through an inside of the sampling target region is equal to or greater than a predetermined ratio with respect to a length of the recommended path in the sampling target region, the processor is configured to determine that the tissue sampling needle has passed through the sampling target region.

8. The ultrasound diagnostic apparatus according to claim 2, wherein in a case where a length of the tissue sampling needle, which is detected, having passed through an inside of the sampling target region is equal to or greater than a predetermined ratio with respect to a length of the recommended path in the sampling target region, the processor is configured to determine that the tissue sampling needle has passed through the sampling target region.

9. The ultrasound diagnostic apparatus according to claim 1, wherein the processor is further configured to issue a warning in a case where it is predicted that the tissue sampling needle detected advances toward pectoralis major muscle of the subject.

10. The ultrasound diagnostic apparatus according to claim 1, wherein the processor is further configured to determine whether or not the tissue sampling needle has reached a piercing final point based on the detection of the tissue sampling needle.

11. The ultrasound diagnostic apparatus according to claim 10, further comprising:

an examination result memory configured to store
a first ultrasound image acquired before the tissue sampling needle passes through the sampling target region,
a second ultrasound image, coordinates of the tissue sampling needle, or a third ultrasound image of the detected tissue sampling needle, which are acquired or detected at a time when it is determined that the tissue sampling needle has reached the final point, and
a fourth ultrasound image including the sampling target region acquired after the tissue sampling needle is pulled out from the subject,
wherein the first ultrasound image, the second ultrasound image, the third ultrasound image and the fourth ultrasound image are included in the plurality of ultrasound images.

12. The ultrasound diagnostic apparatus according to claim 1, wherein the processor is configured to acquire the plurality of ultrasound images in both a cross section including the recommended path and a cross section orthogonal to the cross section including the recommended path.

13. The ultrasound diagnostic apparatus according to claim 1, wherein the processor is configured to acquire a three-dimensional ultrasound image separately from acquiring the plurality of ultrasound images.

14. The ultrasound diagnostic apparatus according to claim 13, wherein the processor is configured to calculate a volume of the detected sampling target region, and displays the volume on the monitor.

15. The ultrasound diagnostic apparatus according to claim 1, wherein the processor is configured to
detect the sampling target region based on a fifth ultrasound image acquired before the piercing of the tissue sampling needle, and
detect again the sampling target region based on a sixth ultrasound image acquired after the tissue sampling needle retreats from the sampling target region,
where the fifth ultrasound image and the sixth ultrasound image are included in the plurality of ultrasound images.

16. The ultrasound diagnostic apparatus according to claim 1, wherein the processor is further configured to
detect deflection occurring in a path through which the tissue sampling needle has passed in the plurality of ultrasound images based on the detection of the tissue sampling needle; and
emphasize a continuous region having a brightness value within a predetermined range for a brightness value of each of the plurality of ultrasound images for a position where the deflection is detected, as a deflection occurrence region, and displays the deflection occurrence region on the monitor.

17. A control method of an ultrasound diagnostic apparatus, the control method comprising:

acquiring a plurality of ultrasound images in which a breast of a subject is captured;
determining a malignancy value in each of a plurality of portions in a region of interest of the breast of the subject in the plurality of ultrasound images by analyzing the plurality of ultrasound images;
calculating a malignancy threshold value by multiplying a predetermined ratio to a maximum value of the malignancy values;
detecting a region in which the malignancy value is greater than or equal to the malignancy threshold value as a sampling target region in which a tissue is sampled from the subject by a tissue sampling needle based on each of the plurality of ultrasound images;
calculating a recommended path of the tissue sampling needle passing through the sampling target region;
displaying the plurality of ultrasound images sequentially on a monitor;
displaying the recommended path superimposed on each of the plurality of ultrasound images on the monitor;
detecting a location of a distal end of the tissue sampling needle in at least one of the plurality of ultrasound images;
based on detecting the location of the distal end of the tissue sampling needle, making a determination that the distal end of the tissue sampling needle enters the sampling target region from an entry point on a contour of the sampling target region and then exits the sampling target region from an exit point on the contour different from the entry point; and
after the determination, notifying an examiner that the tissue sampling needle has passed through the sampling target region.

* * * * *